United States Patent [19]
Boone et al.

[11] Patent Number: 5,606,024
[45] Date of Patent: Feb. 25, 1997

[54] CANINE G-CSF POLYPEPTIDES AND PHARMACEUTICAL COMPOSITIONS COMPRISING SAME

[75] Inventors: Thomas C. Boone, Newbury Park; Allan L. Miller, Glendale, both of Calif.

[73] Assignee: Amgen Inc., Thousand Oaks, Calif.

[21] Appl. No.: 428,732

[22] Filed: Apr. 24, 1995

Related U.S. Application Data

[62] Division of Ser. No. 255,206, Jun. 7, 1994, abandoned, which is a continuation of Ser. No. 826,288, Jan. 27, 1992, abandoned, which is a continuation of Ser. No. 420,038, Oct. 10, 1989, abandoned.

[51] Int. Cl.$^6$ .................... C07K 14/535; A61K 45/05
[52] U.S. Cl. .......................................... 530/351; 424/85.1
[58] Field of Search .................... 530/350, 351; 424/85.1; 435/69.5, 172.3, 252.3

[56] References Cited

U.S. PATENT DOCUMENTS

| | | | |
|---|---|---|---|
| 4,810,643 | 3/1989 | Souza | 435/68 |
| 5,472,857 | 12/1995 | Boone et al. | 435/69.5 |

FOREIGN PATENT DOCUMENTS

| | | |
|---|---|---|
| 0220520A1 | 5/1987 | European Pat. Off. |
| 9105798 | 5/1991 | WIPO. |

OTHER PUBLICATIONS

Tsuchiya et al, "Isolation and Characterization of the cDNA for Murine Granulocyte Colony–Stimulating Factor", *Immunobiology* 172: 175–184 (1986).

Nagata et al., "The chromosomal gene structure and two mRNAs for human granulocyte colony–stimulating factor", *EMBO Journal*, 5(3): 575–581 (Mar. 1986).

Tsuchiya et al, "Characterization of recombinant human granulocyte colony–stimulating factor produced in mouse cells", *EMBO Journal*, 6(3): 611–616 (1987).

Neumeier and Maurer, "Isolation of a High Molecular Mass Granulocyte Colony–Stimulating Factor from Bovine Lung Conditioned Medium", *Hoppe Seyler's Z. Physiol. Chemistry*, 363: 1493–1500 (Dec. 1982).

Schuening et al., "Effect of Recombinant Granulocyte Colony–Stimulating Factor on Hematopoiesi of Normal Dogs and on Hematopoietic Recovery After Otherwise Lethal Total Body Irradiation", *Blood*, 74: 1308–1313 (1989).

Lothrop et al, "Correction of canine cyclic hematopoiesis with recombinant human granulocyte colony–stimulating factor", *Chemical Abstracts*, 109: 642–643 (1988).

Matsumoto, "Protective Effect of Human Granulocyte Colony–Stimulating Factor on Microbial Infection in Neutropenic Mice", *Infection and Immunity*, 55: 2715–2720 (1987).

Metcalf. 1991. Phil. Trans. R. Soc. Lond. B 333:147–173.

Hollingshead et al. 1991. Drugs 42:300–330.

Lothrop et al. 1988. Blood 72:1324–1328.

Pratt et al. 1990. Exp. Hematol. 18:1199–1203.

Scheuning et al. 1990. Blood 76:636–640.

Kurzman et al. 1992. Mol. Biotherm. 4:29–33.

Hammond et al. 1990. Blood 76:523–32.

Mishu et al. 1992. JAVMA 200:1957–1964.

Obradovich et al. 1991. J. Vet. Int. Med. 5:75–79.

*Primary Examiner*—Stephen G. Walsh
*Assistant Examiner*—Elizabeth C. Kemmerer
*Attorney, Agent, or Firm*—Craig A. Crandall; Steven M. Odre; Ron K. Levy

[57] ABSTRACT

Compositions and methods for treating or preventing infections in canine or feline animals which comprises administering an effective amount of granulocyte colony stimulating factor (G-CSF), are disclosed. The G-CSF may be naturally derived, or alternatively, the G-CSF and genetically engineered variants of G-CSF may be the expression products of genetically engineered prokaryotic or eukaryotic host cells.

4 Claims, 16 Drawing Sheets

Restriction Map of Canine G-CSF

```
Ala Pro Leu Gly Pro Thr Gly Pro Leu Pro Gln Ser Phe Leu Leu
gcc ccc ctg ggc cct acc ggc ccc ctg ccc cag agc ttc ctg ctc Lys Cys Leu Glu Gln Met Arg Lys Val Gln Ala Asp Gly Thr Ala
aag tgc cta gag caa atg agg aag gtc cag gct gat ggc acg gcg Leu Gln Glu Thr Leu Cys Ala Thr His Gln Leu Cys His Pro Glu
ctg cag gag acg ctg tgt gcc acc cac cag ctg tgc cat cct gag Glu Leu Val Leu Leu Gly His Ala Leu Gly Ile Pro Gln Pro Pro
gag ttg gtg ctg ctc ggg cac gct ggc atc ccc cag cct ccc Leu Ser Ser Cys Ser Ser Gln Ala Leu Gln Leu Met Gly Cys Leu
ctg agc agc tgc tcc agc cag gcc ctg cag ctg atg ggc tgc ctg Arg Gln Leu His Ser Gly Leu Phe Leu Tyr Gln Gly Leu Leu Gln
cgt caa ctc cac agc ggc ctc ttc ctc tac cag ggc ctc ctg cag
```

FIG. 2-A

```
Ala Leu Ala Gly Ile Ser Pro Glu Leu Ala Pro Thr Leu Asp Thr
gcc ctg gca ggg ata tcc ccc gag tta gcg ccc acc ttg gac aca Leu Gln Leu Asp Thr Thr Asp Phe Ala Ile Asn Ile Trp Gln Gln
ctg cag ctg gac acc acc gac ttt gcc atc aac atc tgg cag cag Met Glu Asp Leu Gly Met Ala Pro Ala Val Pro Pro Thr Gln Gly
atg gaa gat cta gga atg gcc ccc gcc gtg cca cct acc cag ggc Thr Met Pro Ala Phe Thr Ser Ala Phe Gln Arg Arg Ala Gly Gly
acc atg cca gcc ttc acc tcg gcc ttc cag cgc cgg gca gga ggt Val Leu Val Ala Ser Asn Leu Gln Ser Phe Leu Glu Leu Ala Tyr
gtc ctg gtg gcc tcc aac ctg cag agc ttc ctg gag ctg gca tat Arg Ala Leu Arg His Phe Ala Lys Pro
cgc gct ctg cgc cac ttt gcc aaa ccc
```

FIG. 2-B

```
GGGGACAGGCTTGAGAATCCCAAAGGAGAGGGCAAGGACACTGCCCCCGCAAGTCTGCCAGAGCAGTCTGCCACTTCCC      100

CACAGGCTCGTGCCGCTTCCAGGCGTCTATCAGCGGCTCAGCCTTGTTCAGCTGTCTGTTCAAACACTCTGGGCCTGGGGCAGC  200

GGGAAGGAGTTTGAGGGGCAAGGCGACGTCAAAGGAGGATCAGAGATTCCACAATTTCGCAAAACAGCTTTTTGTTCCAACCCC  300

CCTGCATTGTCTTGGACACCAAATTTGCATAAATCCTGGGAAGTTATTACTAAGCCTTAGTCGTGGCCCCAGGTAATTCCTCCCAGGCCTCCATGGGGT 400
                                                                        -30
                                                                        MetAlaGlyProAlaThrGlnSerProM
TATGTATAAAGGGCCCCCTAGAGCTGGGCCCCAAAACAGCCCGGAGCCTGCAGCCCCACCCAGACCTGGACCTGCACCCAGAGCCCCA          500
    -20  -18
    etLysLeuMetA
    TGAAGCTGATGGGGTGAGTGTCTTGGCCCCAGGATGGGAGAGGCCGCTCCCTGGCATGGGGAGGGGCTGGGTGTGACAGAGGGGCTGGGGATCCCCGTTCT  600
                                                                                        -16
                                                                                        laLeuGlnLeuL
                                                                                        CCCTGCCAGCTGC

GGGAATGGGGATTAAAGGCACCCAGTGTCCCCGAGAGGGCCTCAGTGGTAGGGAACAGCATGTCTCCTGAGCCCGCTCTGTCCCAGCCCTGCCAGCTGC  700
                                                                                10
                                                                                euLeuTrpHisSerAlaLeuTrpThrValGlnGluAlaThrProLeuGlyProAlaSerSerLeuProGlnSerPheLeuLeuLysCysLeuGluGlnVa
                                                                                TGCTGTGGCACAGTGCACTCTGGACAGTGCCAGGAAGCCAGCCCCTGCCCAGAGCTTCCTGCTCAAGTGCTTAGAGCAAGT 800
    30                                      35
lArgLysIleGlnGlyAspGlyAlaAlaLeuGlnGluLysLeu
GAGGAAGATCCAGGGCGATGGGGCAGCGCTCCAGGAAGCTGGTGAGTGAGGTGGGTGAGAGGGCTGTGGAGGGAAGCCCGGTGGGGAGAGCTAAGGGG      900
```

FIG. 3-A

```
GATGGAACTGCAGGGCCAACATCCTCTGGAAGGGACATGGGAGCAGTGGAGGCTGGGGAAGGCTGGGGGAGGACTT GGGGGAGGAGGACCT  1000

TGGTGGGACAGTGCTCGGGGAGGCTGGCTGGGATGGAGGCATCACATTCAGGAGACATCAGGAAAGGGCAAGGGCCCCTGTGAGATCAGAGAGTGGGGGTG  1100

CAGGGCAGAGAGGAACTGAACAGCCTGGCAGGACAGAGAGTCGGGGAGGACCCGGGAAGGAGGCGGCGACCCGGCCACGGC  1200
                                      36
                                      CysAlaThrTyrLysLeuCysHisProGluGluLeuValLeuLeuGlyHisSerLeuGlyIleProTrpA
GAGTCTCACTCAGCATCCTTCCATCCCCAGTGTGCCACTACAAGCTGTGCCACCCCGAGGAGCTCGGACACTCTGGGCATCCCCCTGGG  1300
         60                          70 71
         laProLeuSerSerCysProSerGlnAlaLeuGlnLeu
CTCCCCGAGGCAGCAGCTGCCCCAGCCAGGCCCTGCAGCTGGTGAGTGTCAGGAAAGGATAAGGCTAATGAGGAGGGGAAGGAGGAGGAACACCCATGGG  1400
                                                                                      72
                                                                                      AlaGlyCysLeuSerGln
CTCCCCCATGTCTCCAGGCTGGGGGCCTGACGTATCTCAGGCAGCACCCCCTAACTCTTCCGCTCTGTCTCACAGGCAGGCTGCTTGAGCCAA  1500
         80                              90                           100                     110
         LeuHisSerGlyLeuPheLeuTyrGlnGlyLeuLeuGlnAlaLeuGluGlyIleSerProGluLeuGlyProThrLeuAspThrLeuGlnLeuAspValA
CTCCATAGCGGCCCTTTCCTCTCTACCAGGCCCTGGAAGGGATCTCCCCGAGTTGGGTCCCACCTTGGACACTCGACAGCTGGACGTCG  1600
         120
         laAspPheAlaThrThrIleTrpGlnGln
CCGACTTTGCCACCACCATCTGGCAGCAGGTGAGCCCTTGTTGGGCAGGTGGGCCAAGGTGTCGTCGTGCTGCTGGCATTCTGGGCACCACCAGCCGGGGCCTGTGTATGG  1700
```

FIG. 3-B

```
                                                                                               1800
GCCCTGTCCATGCTGTCAGCCCCCAGCATTTCCTCATTTGTAATAACGCCCACTCAGAAGGGCCCAACCACTGATCACAGCTTTCCCCACAGA┌ATGGAAG
                                                                                            121│
                                                                                            MetGluG│ 1900
       130                                        140                                 174   │
 luLeuGlyMetAlaProAlaLeuGlnProThrGlnGlyAlaMetProAlaPheAlaSerAlaPheGlnArgArgAlaGlyValGlyValLeuValAlaSerHi│
AACTGGGAATGGCCCCTGCCCTGCAGCCCCACCCAGGGTGCCAGCCGGCCTTCGCTTTCCAGCGCCGGGCAGGAGGGGTCCTGGTTGCCTCCCA│
                                                                                               │ 2000
      160                           170             174                                        │
 sLeuGlnSerPheLeuGluValSerTyrArgValLeuArgHisLeuAlaGlnProOP                                      │
TCTGCAGAGCTTCCTGGAGGTGTCGTACCGCGTTCTACGCCACCTTGCCCAGCCCCTGAGCCAAGCCCTCTGTCCTTCCCTGCATTTCTGAGTTTCATTCCTGCC│
                                                                                               │ 2100
TTATGTCTATTTAAGCCTCATATTTAAAGACAGGAAGACAGAACCCCAGGAGCCCACTCCCCATCCCCTGGACTGGGAGGTAGATAGGTAAATACCAAGTATTTATTACTATGACTGCTCCCCAGCCCTGG│
                                                                                               │ 2200
TGTAGCAGTGAGAAAAAGCTCCTGTCCGTGAGCCGCTGTGAGCCCTGGTCCTGAGGGTCCCGAGGGTCCCCACCCTGGACCTCAGGTATCCAGTCCACAGCCCCTGCATCCCCTT│
                                                                                               │ 2300
CTCTGCAATGGGCACTGGGATGAGCCAGTAGCCAGAGGTGGCCAGAGCATGGCCCTGGGTCCCAGCGACTGCTGGGGAATCGCTGTGGGGAATCTCGTTTTCTTCTTAAGAC│
                                                                                               │ 2400
AAATCCCTGTTTAATATTTAAACAGCAGAGGTGGCCAGAGCATGGCCCTGGGTCCCAGCGACTGCACAGCGGGCCCTGCATCCCCTT│
                                                                                               │ 2500
GGCTGTGAGGCCCTGGACTCCCGAACATCACGACGTGTCTCCTGTTTTTCGGGTGGCTCGGGACACCTGCCCTGCCCCCACGAGGGTCAGGACTGT│
                                                                                               │ 2600
TTTGGGACATGGTTTGACTCCCGAACATCACGACGTGTCTCCTGTTTTTCGGGTGGCTCGGGACACCTGCCCTGCCCCCACGAGGGTCAGGACTGT│
                                                                                               │ 2700
GACTCTTTTAGGGCAGGCAGGTGCCTGGACATTTGCCTGGGACTGTGGGAGGGAGCAGACAGGAGGAATCATGTCAGGCCTGT│
                                                                                               │ 2800
GTGTGAAAGGAAGCTCCACTGTCACCCTCTTCACCCCCACTGTCACATTGTAACTGAACTTCAGGATAATAAAG│
                                                                                               │ 2900
TGTTTGCCTCCCA└GTCACGTCCTTCCTCCTTCTTGAGTCCAGTGGTGCTGGCCAGGGCTGGGAGGTGGCTGAAGGGTGGGAGAGGCCAGAGGAGGT
                                                                                               3000
CGGGAGGAGGTCTGGGGAGGAGGTCCAGGGAGGAGGAGAAAGTTCTCAAGTTCGTCTGACATTCATTCCGTTAGCACATATTTATCTGAGCACCTACT
                                                                                               3070
CTGTGCAGACGCTGGGCTAAGTGCTGGGGACAGCAGGAACAGGAACAGGAACAGACATGGAATCTGCACTCGAG
```

FIG. 3-C

```
  C TAG AAA AAA CCA AGG AGG TAA TAA ATA ATG GCA CCT TTA GGT CCA ACT GGT CCT CTG
                                      30                                     60
                                         Met Ala Pro Leu Gly Pro Thr Gly Pro Leu

CCT CAA AGT TTC CTG CTG AAA TGC CTC GAG CAG ATG CGT AAA GTT CAA GCT GAT GGT ACC
                                     90                                     120
Pro Gln Ser Phe Leu Leu Lys Cys Leu Glu Gln Met Arg Lys Val Gln Ala Asp Gly Thr

GCA CTC CAA GAA ACT CTG TGC GCA ACT CTG TGC CAC CAA CTG CAA CTC CCT GAA GAA CTC GTA CTG
                                    150                                     180
Ala Leu Gln Glu Thr Leu Cys Ala Thr Leu Cys His Gln Leu Gln Leu Pro Glu Glu Leu Val Leu

CTC GGT CAC GCA CTC GGT ATT CCG CAG CCG CTG TCT TCT TGC TCC TCT CAG GCT CTG
                                    210                                     240
Leu Gly His Ala Leu Gly Ile Pro Gln Pro Leu Ser Ser Cys Ser Ser Gln Ala Leu

CAA CTC ATG GGT TGC CTC CGT CAA CTG CAT TCT GGC CTG TTC CTG TAC CAG GGT CTC CTG
                                    270                                     300
Gln Leu Met Gly Cys Leu Arg Gln Leu His Ser Gly Leu Phe Leu Tyr Gln Gly Leu Leu
```

FIG. 4-A

```
CAA GCT TTG GCT GGC ATC TCT CCG GAA CTC GCA CCT ACT CTC GAC ACT CTG CAG CTC GAC
Gln Ala Leu Ala Gly Ile Ser Pro Glu Leu Ala Pro Thr Leu Asp Thr Leu Gln Leu Asp
                                330                              360

ACT ACC GAC TTC GCT ATC AAC ATT TGG CAG CAA ATG GAA GAT CTG GGC ATG GCA CCG GCT
Thr Thr Asp Phe Ala Ile Asn Ile Trp Gln Gln Met Glu Asp Leu Gly Met Ala Pro Ala
                                390                              420

GTT CCG CCG ACT CAG GGC ACT ATG CCT TTT ACT TCT GCT TTC CAG CGT CGT GCT GGT
Val Pro Pro Thr Gln Gly Thr Met Pro Phe Thr Ser Ala Phe Gln Arg Arg Ala Gly
                                450                              480

GGT GTA CTC GTA GCT TCT AAC CTC CAG TCT TTC CTC GAA CTC GCT TAC CGT GCT CTG CGT
Gly Val Leu Val Ala Ser Asn Leu Gln Ser Phe Leu Glu Leu Ala Tyr Arg Ala Leu Arg
                                510                              540

CAC TTC GCT AAA CCG TAA TAG GAT C
His Phe Ala Lys Pro End End Asp
```

FIG. 4-B

```
         10         20         30         40         50         60
CTAGAAAA   AACCAAGGAG GTAATAAATA ATGGCACCTT TAGGTCCAAC TGGTCCTCTG
TTTT       TTGGTTCCTC CATTATTTAT TACCGTGGAA ATCCAGGTTG ACCAGGAGAC
xbaI 70         80         90        100        110        120
CCTCAAAGTT TCCTGCTGAA ATGCCTCGAG CAGATGCGTA AAGTTCAAGC TGATGGTACC
GGAGTTTCAA AGGACGACTT TACGGAGCTC GTCTACGCAT TTCAAGTTCG ACTACCATGG 130        140        150        160        170        180
GCACTCCAAG AAACTCTGTG CGCAACTCAC CAACTGTGCC ACCCTGAAGA ACTCGTACTG
CGTGAGGTTC TTTGAGACAC GCGTTGAGTG GTTGACACGG TGGGACTTCT TGAGCATGAC 190        200        210        220        230        240
CTCGGTCACG CACTCGGGTAT TCCGCAGCCG CCGCTGTCTT CTTGCTCCTC TCAGGCTCTG
GAGCCAGTGC GTGAGCCATA AGGCGTCGGC GGCGACAGAA GAACGAGGAG AGTCCGAGAC 250        260        270        280        290        300
CAACTCATGG GTTGCCTCCG TCAACTGCAT TCTGGCCTGT TCCTGTACCA GGGTCTCCTG
GTTGAGTACC CAACGGAGGC AGTTGACGTA AGACCGGACA AGGACATGGT CCCAGAGGAC
```

FIG. 5-A

```
      310         320         330         340         350         360
CAAGCTTTGG CTGGCATCTC TCCGGAACTC GCACCTACTC TCGACACTCT GCAGCTCGAC
GTTCGAAACC GACCGTAGAG AGGCCTTGAG CGTGGATGAG AGCTGTGAGA CGTCGAGCTG
     HindIII
      370         380         390         400         410         420
ACTACCGACT TCGCTATCAA CATTTGGCAG CAAATGGAAG ATCTGGGCAT GGCACCGGCT
TGATGGCTGA AGCGATAGTT GTAAACCGTC GTTTACCTTC TAGACCCGTA CCGTGGCCGA 430         440         450         460         470         480
GTTCCCGCCGA GTCAGGGCAC TATGCCTGCT TTTACTTCTG CTTCCAGCG TCGTGCTGGT
CAAGGGCGGCT GAGTCCCGTG ATACGGACGA AAATGAAGAC GAAAGGTCGC AGCACGACCA 490         500         510         520         530         540
GGTGTACTCG TAGCTTCTAA CCTCCAGTCT TTCCCTCGAAC TCGCTTACCG TGCTCTGCGT
CCACATGAGC ATCGAAGATT GGAGGTCAGA AAGGAGCTTG AGCGAATGGC ACGAGACGCA 550         560
CACTTCGCTA AACCGTAATA G   BamH1
GTGAAGCGAT TTGGCATTAT C CCTAG
```

FIG. 5-B

```
         10         20         30         40         50         60
CTAGAAAAAA CCAAGGAGGT AATAAATAAT GGCACCTTTA GGTCCAACTG GTCCTCTGCC
GATCTTTTTT GGTTCCTCCA TTATTTATTA CCGTGGAAAT CCAGGTTGAC CAGGAGACGG
 xbaI 70         80         90        100        110        120
TCAAAGTTTC CTGCTGAAAT GCCTCGAGCA GATGCGTAAA GTTCAAGCTG ATGGTACCGC
AGTTTCAAAG GACGACTTTA CGGAGCTCGT CTACGCATTT CAAGTTCGAC TACCATGGCG 130        140        150        160        170        180
ACTCCAAGAA ACTCTGTGCG CAACTCACCA ACTGTGCCAC CCTGAAGAAC TCGTACTGCT
TGAGGTTCTT TGAGACACGC GTTGAGTGGT TGACACGGTG GGACTTCTTG AGCATGACGA 190        200        210        220        230        240
CGGTCACGCA CTCGGTATTC CGCAGCCGCC GCTGTCTTCT TGCTCCTCTC AGGCTCTGCA
GCCAGTGCGT GAGCCATAAG GCGTCGGCGG CGACAGAAGA ACGAGGAGAG TCCGAGACGT 250        260        270        280        290        300
ACTCATGGGT TGCCTCCGTC AACTGCATTC TGGCCTGTTC CTGTACCAGG GTCTCCTGCA TCGA
TGAGTACCCA ACGGAGGCAG TTGACGTAAG ACCGGACAAG GACATGGTCC CAGAGGACGT
                                                              HindIII
```

FIG. 6-A

```
        10         20         30         40         50         60
AGCTTTGGCT GGCATCTCTC CGGAACTCGC ACCTACTCTC GACACTCTGC AGCTCGACAC
AACCGA     CCGTAGAGAG GCCTTGAGCG TGGATGAGAG CTGTGAGACG TCGAGCTGTG
   HindIII 70         80         90        100        110        120
TACCGACTTC GCTATCAACA TTTGGCAGCA AATGGAAGAT CTGGGCATGG CACCGGCTGT
ATGGCTGAAG CGATAGTTGT AAACCGTCGT TTACCTTCTA GACCCGTACC GTGGCCGACA 130        140        150        160        170        180
TCCGCCGACT CAGGGCACTA TGCCTGCTTT TACTTCTGCT TTCCAGCGTC GTGCTGGTGG
AGGCGGCTGA GTCCCGTGAT ACGGACGAAA ATGAAGACGA AAGGTCGCAG CACGACCACC 190        200        210        220        230        240
TGTACTCGTA GCTTCTAACC TCCAGTCTTT CCTCGAACTC GCTTACCGTG CTCTGCGTCA
ACATGAGCAT CGAAGATTGG AGGTCAGAAA GGAGCTTGAG CGAATGGCAC GAGACGCAGT 250        260
CTTCGCTAAA CCGTAATAG
GAAGCGATTT GGCATTATCC TAG
                BamH1
```

FIG. 6-B

```
 1  MetAlaProLeuGlyProThrGlyProLeuProGlnSerPheLeuLeuLysCysLeuGlu
 1  MetThrProLeuGlyProAlaSerSerLeuProGlnSerPheLeuLeuLysCysLeuGlu

21  GlnMetArgLysValGlnAlaAspGlyThrAlaLeuGlnThrLeuCysAlaThrHis
21  GlnValArgLysIleGlnGlyAspGlyAlaAlaLeuGlnGluLysCysAlaThrTyr

41  GlnLeuCysHisProGluGluValLeuLeuGlyHisAlaLeuGlyIleProGlnPro
41  LysLeuCysHisProGluGluValLeuLeuGlyHisSerLeuGlyIleProTrpAla

61  ProLeuSerSerCysSerSerGlnAlaLeuGlnLeuMetGlyCysLeuArgGlnLeuHis
61  ProLeuSerSerCysProSerGlnAlaLeuGlnLeuAlaGlyCysLeuSerGlnLeuHis

81  SerGlyLeuPheLeuTyrGlnGlyLeuLeuGlnAlaLeuAlaGlyIleSerProGluLeu
81  SerGlyLeuPheLeuTyrGlnGlyLeuLeuGlnAlaLeuGluGlyIleSerProGluLeu
```

FIG. 7-A

```
101  AlaProThrLeuAspThrThrAspPheAlaIleAsnIleTrpGln
101  GlyProThrLeuAspThrThrAspPheAlaIleAsnIleTrpGln
121  GlnMetGluAspLeuGluGlyMetAlaProAlaValProProThrGlnGlyThrMetProAla
121  GlnMetGluGluLeuGluGlyMetAlaProAlaLeuGlnProThrGlnGlyAlaMetProAla
141  PheThrSerAlaPheGlnArgArgAlaGlyGlyValLeuValAlaSerAsnLeuGlnSer
141  PheAlaSerAlaPheGlnArgArgAlaGlyGlyValLeuValAlaSerHisLeuGlnSer
161  PheLeuGluLeuAlaTyrArgAlaLeuArgHisPheAlaLysPro
161  PheLeuGluValSerTyrArgValLeuArgHisLeuAlaGlnPro
```

FIG. 7-B

CANINE G-CSF POLYPEPTIDES AND PHARMACEUTICAL COMPOSITIONS COMPRISING SAME

This application is a division of application Ser. No. 08/255,206, filed Jun. 7, 1994, now abandoned, which in turn is a continuation of application Ser. No. 07/826,288, filed Jan. 27, 1992, now abandoned, which in turn is a continuation of application Ser. No. 07/420,038, filed Oct. 10, 1989, now abandoned.

FIELD OF THE INVENTION

The present invention is directed to the use of granulocyte colony stimulating factor (G-CSF) to treat or prevent infections in canine and feline animals. More specifically, the invention is directed to the use of G-CSF having the amino acid sequence of human G-CSF or having the amino acid sequence of canine G-CSF, in treating or preventing infections in canine or feline animals. The source of the G-CSF may be naturally derived or may be derived from genetically engineered prokaryotic or eukaryotic host cells containing recombinant plasmid or viral DNA vectors carrying the human or canine G-CSF gene, or genetically engineered variants of canine G-CSF genes, or synthetic human or canine G-CSF genes. The present invention is also directed to DNA gene segments, biologically functional recombinant plasmids and viral DNA vectors, and prokaryotic and eukaryotic host cells containing such recombinant plasmids and vectors, all of which contain a canine G-CSF gene or a genetically engineered variant of a canine G-CSF gene.

BACKGROUND OF THE INVENTION

Although antibiotic therapy is now used for animal infections with some success, huge losses persist. The early hopes that antibiotics would allow complete control of the disease have not been realized. None of the antibiotics utilized thus far has been entirely satisfactory. Additionally, it has been found to be very desirable to replace antibiotic treatment with treatment by non-antibiotic chemo-therapeutic drug compounds, for the following reasons:

(1) Antibiotics effective in human medicine should not be utilized in veterinary medicine, in order not to build up strain resistance of bacteria appearing in human diseases; and (2) Antibiotics should be reserved for such diseases for which no chemo-therapeutic drug compound would be available, as it has been proved that bacterial strains build up resistance to an antibiotic after extended use of such antibiotic.

Despite these several published methods, it remains very important to find cost-effective methods utilizing non-antibiotic compounds which would substantially overcome the drawbacks of antibiotics used thus far and yet would be effective in treating and preventing infections in canine and feline animals.

Canine parvo virus still infects over one-half million young dogs. Hospitalization and intensive care are required. Mortality occurs in 15–20% of the cases. Severe neutropenia occurs and death is thought to frequently result from secondary infections and sepsis.

Feline Immunedeficiency Virus (FIV) is believed to infect 500,000–1,000,000 cats per year. This virus causes neutropenia in approximately 30% of the cats which renders them susceptible to infections. Feline Leukemia Virus (FeLV) also causes neutropenia in cats.

Granulocyte Colony Stimulating Factor

Granulocyte colony stimulating factor (G-CSF) is one of several glycoprotein growth factors known as colony stimulating factors (CSFs) because they support the proliferation of haemopoietic progenitor cells. G-CSF stimulates the proliferation of specific bone marrow precursor cells and their differentiation into granulocytes. It is distinguished from other CSFs by its ability to both stimulate neutrophilic granulocyte colony formation in semi-solid agar and to induce terminal differentiation of murine myelomonocytic leukemic cells in vitro. The cDNA cloning and expression of recombinant human G-CSF has been described, and it has been confirmed that the recombinant G-CSF exhibits most, if not all, of the biological properties of the native molecule (Souza, L. et al. Science 232, 61–65 (1986)). Sequence analysis of the cDNA and genomic DNA clones has allowed the deduction of the amino acid sequence and reveals that the protein is 204 amino acids long with a signal sequence of 30 amino acids. The mature protein is 174 amino acids long and possesses no potential N-linked glycosylation sites but several possible sites for O-linked glycosylation.

The cloning and expression of cDNA encoding human G-CSF has been described by two groups (Nagata, S. et. al., Nature 319, 415–418 (1986); Souza, L. M. et al., Science 232, 61–65 (1986)). The first report of a G-CSF cDNA clone suggested that the mature protein was 177 amino acids in length. The authors reported that they had also identified a cDNA clone for G-CSF that coded for a protein that lacked a stretch of three amino acids. This shorter form of G-CSF cDNA expresses the expected G-CSF activity. The second report describes a cDNA sequence identical to this short form and makes no mention of other variants. Since these authors confirmed that the short cDNA expresses G-CSF with the expected profile of biological activity, it is probable that this is the important form of G-CSF and that the longer form is either a minor splicing variant or the result of a cloning artifact.

Matsumoto et al., in Infection and Immunity, Vol. 55, No. 11, p. 2715 (1987) discuss the protective effect of human G-CSF on microbial infection in neutropenic mice.

The following patent publications relate to G-CSF: WO-A-8703689, assigned to Kirin/Amgen describes hybridomas producing monoclonal antibodies specific for G-CSF and their use in the purification of G-CSF; WO-A-8702060, assigned to Biogen, discloses human G-CSF like polypeptides and methods of producing them; U.S. Pat. No. 4,810,643 assigned to Amgen, discloses human G-CSF like polypeptides, sequences encoding them and methods of their production; and WO-A-8604605 and WO-A-8604506, both asigned to Chugai Seiyaku Kabushiki Kaisha, disclose a gene encoding human G-CSF and infection inhibitors containing human G-CSF.

The use of recombinant G-CSF with the same amino acid sequence as human G-CSF, in dogs with cyclic neutropenia has been associated with the development of neutralizing antibodies to the heterologous G-CSF protein during a thirty day period of administration (see Lothtop et al., Blood 72, 5624–37 (1988). Subsequent treatment of these same dogs with recombinant human GM-CSF failed to cause a significant leukocytosis or eliminate cycles of neutropenia. A significant variation in structure may explain the development of neutralizing antibodies when the human sequence products are given to dogs. The development of neutralizing antibodies in dogs given the human sequence products may limit them to single or short term use.

It is an object of the subject invention to provide an improved method of treating and preventing infections in canine or feline animals.

It is a further object of the subject invention to provide a method of treating infections in canine or feline animals without build up of strain resistance of bacteria.

A still further object of the invention is to provide a purified and isolated polypeptide having part or all of the primary structural conformation and the biological properties of naturally occurring canine G-CSF, and DNA sequences encoding such G-CSF.

Other objects, features and characteristics of the present invention will become apparent upon consideration of the following description and the appended claims.

SUMMARY OF THE INVENTION

The present invention provides DNA sequences, biologically functional recombinant plasmids and viral DNA vectors, and prokaryotic and eukaryotic host cells containing such recombinant plasmids and vectors, all of which contain a canine G-CSF gene or a genetically engineered variant of a canine G-CSF gene. The invention also provides polypeptides encoded by the canine G-CSF gene or variants thereof. A method for treating or preventing infections in canine or feline animals is also disclosed.

Novel DNA sequences of the invention include sequences useful in securing expression in prokaryotic or eukaryotic host cells of polypeptide products having at least a part of the primary structural conformation and the biological properties of naturally occurring canine granulocyte colony stimulating factor. DNA sequences of the invention are specifically seen to comprise the DNA sequence of the coding region of the mature protein, set forth in FIG. 2 or its complimentary strand, allelic variant forms of canine G-CSF, manufactured DNA sequences encoding canine G-CSF, fragments of canine G-CSF and analogs of canine G-CSF with DNA sequences incorporating codons facilitating translation of messenger RNA in microbial hosts. Such manufactured sequences may readily be constructed according to the methods of Alton, et al., PCT published application WO 83/04053.

A further embodiment of the invention relates to synthetic genes designed to allow for expression of G-CSF having the canine amino acid sequence in *E. coli*.

Also comprehended by the invention are pharmaceutical compositions comprising effective amounts of polypeptide products of the invention together with suitable diluents, adjuvants and/or carriers useful in animal therapy.

The subject invention also relates to a method for treating and preventing infections in canine or feline animals by administering a therapeutically effective treating or preventing amount of granulocyte colony stimulating factor, advantageously G-CSF derived from the gene of a canine animal. In addition, the invention relates to a method of treating cancer in canine or feline animals by administering a therapeutically effective treating or preventing amount of granulocyte colony stimulating factor as an adjunct to chemotherapy.

BRIEF DESCRIPTION OF THE DRAWINGS

FIGS. 2A–2B illustrates the coding region of the mature protein of canine G-CSF (SEQ ID NOS:1 and 2);

FIG. 3 is the genomic sequence of the human-G-CSF (SEQ ID NO:3);

FIGS. 4A–4B is the DNA sequence of a canine G-CSF synthetic gene (cG-CSF dna) (SEQ ID NOS: 4 and 5);

FIGS. 5A–5B illustrates the oligos used to construct the subunits of the canine G-CSF synthetic gene (cG-CSF dna3);

FIGS. 6A and 6B shows the two subunits of the canine G-CSF synthetic gene cG-CSF dna3;

FIGS. 7A–7B shows the homology of canine and human G-CSF (SEQ ID NO: 6).

DETAILED DESCRIPTION OF THE INVENTION

Figure 1:
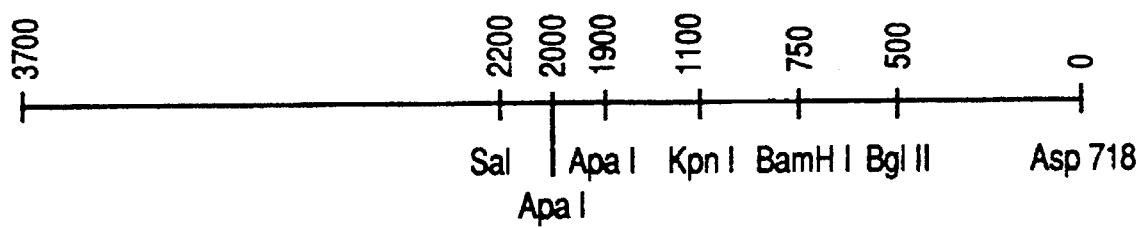
FIG. 1 shows the restriction map of canine G-CSF.

A novel method for treating or preventing infections in canine or feline animals has been discovered. Surprisingly it has been found that G-CSF is effective in a method of treating or preventing infections in canine and feline animals.

The subject invention also relates to treating cancer in dogs or cats by administration of G-CSF as an adjunct to chemotherapy, advantageously, as an adjunct to the use of myelosuppressive drugs. The general method as it applies to humans is described in Gabrilove et al., New England Journal of Medicine 318, No. 22 (1988) hereby incorporated by reference. A skilled veterinarian will adjust the method of administrating dose etc. as appropriate.

A variety of infections afflicting canine and feline animals are treatable by the method of the subject invention. A veterinarian of ordinary skill can readily determine whether an animal exhibits an infection. In one embodiment, the present invention relates to a method of treating or preventing infections such as Feline Immunodeficiency Virus (FIV) in feline animals comprising administering a composition which comprises an effective amount of G-CSF.

In another embodiment of the invention, G-CSF is used to treat Feline Leukemia Virus (FeLV). Additionally G-CSF is used to treat cats with Pan Leukopenia.

In another embodiment dogs infected with Parvo Virus are treated with G-CSF.

The subject invention also relates to the use of G-CSF during bone marrow transplants, G-CSF shortens the time to engraftment (4–7 days vs. 7–10 days in a study with 12 cats).

By "G-CSF" it is meant one of the hematopoietic growth factors known as granulocyte colony stimulating factors. The biological activities of G-CSFs include: stimulating the differentiation of a small number of progenitor "stem cells" into the variety of blood cell lines, stimulating the proliferation of those blood cell lines and stimulating the ultimate differentiation of mature blood cells from those lines. The preferred G-CSF polypeptides for treating or preventing infections in canine or feline animals are human and canine, and may be naturally-derived or the product of genetically engineered host cells containing a DNA sequence encoding G-CSF.

The DNA encoding the G-CSF gene is a genomic DNA sequence, a cDNA sequence or a manufactured (or synthetic) DNA sequence which is expressed in a prokaryotic or eukaryotic host cell as a polypeptide having part or all of the primary structural conformation and the hematopoietic biological properties of naturally-occurring G-CSF. A biologically functional plasmid or viral DNA vector containing a DNA sequence encoding G-CSF may be used to transform or transfect a prokaryotic or eukaryotic host cell to produce cell lines expressing the G-CSF polypeptide, glycosylated or unglycosylated.

The various forms of G-CSF, including their preparation and purification, useful in a method for treating or preventing infections in canine or feline animals commonly owned are described in detail in U.S. Pat. No. 4,810,643, which is hereby incorporated by reference. U.S. Pat. No. 4,810,643 describes and claims novel gene segments, biologically functional recombinant plasmids and viral DNA vectors and prokaryotic and eukaryotic host cells, which contain a G-CSF gene or a genetically engineered variant of a G-CSF gene. The host cells express biologically active G-CSF or a genetically engineered variant of G-CSF.

This application describes the isolation and characterization of a canine G-CSF gene and in particular describes and claims novel gene segments, biologically functional recombinant plasmids and viral DNA vectors, and prokaryotic and eukaryotic host cells, which contain a canine G-CSF gene or a genetically engineered variant of a canine G-CSF gene. The host cells transformed or transfected with the recombinant plasmids or viral DNA vectors express biologically active G-CSF or a genetically engineered variant of G-CSF. The protein expressed is purified using methods known to those skilled in the art.

DNA sequences coding for all or a part of G-CSF having the canine amino acid sequence are provided. Such DNA sequences include: the incorporation of codons "preferred" for expression by selected non-mammalian hosts (e.g. *E. coli* preferred codons, see Nucleic Acids Res. 1986 vol.14 (13) pp 5125–5143); the provision of sites for cleavage by restriction endonuclease enzymes; the provision of DNA sequences which reduce or eliminate secondary structure interactions which inhibit transcription and/or translation; and the provision of additional initial, terminal or intermediate DNA sequences which facilitate incorporation into expression vectors. The DNA sequences of the invention also include sequences having an optimized ribosome binding site, and sequences which enhance transcription, translation, and/or secretion of the protein product.

The present invention also provides DNA sequences coding for expression of polypeptide analogs or derivatives of canine G-CSF which differ from naturally-occurring forms in terms of the identity or location of one or more amino acid residues (i.e., deletion analogs containing less than all of the residues specified for canine G-CSF; substitution analogs, wherein one or more residues specified are replaced by other residues; and in addition, analogs wherein one or more amino acid residues are added to a terminal or medial portion of the polypeptide) and which share the properties of naturally-occurring forms.

Also comprehended by the present invention is that class of polypeptide coded for by portions of the DNA complement to the top strand canine cDNA of FIG. 2, i.e., "complementary inverted proteins" as described by Tramontano, et al., *Nucleic Acids Res.*, 12, 5049–5059 (1984).

The present invention relates to purified and isolated polypeptide products having part or all of the primary structural conformation (i.e., continuous sequence of amino acid residues) and the biological properties (e.g., immunological properties and in vitro biological activity) of naturally-occurring canine G-CSF including allelic variants thereof. These polypeptides are also characterized by being the product of chemical synthetic procedures or of procaryotic or eukaryotic host-expression (e.g., by bacterial, yeast, higher plant, insect and mammalian cells (e.g. CHO or COS) in culture) of exogenous DNA sequences obtained by genomic or cDNA cloning or by gene synthesis. The products of typical yeast (e.g., *Saccaromyces cerevisiae*) or prokaryote [e.g., [*Escherichia coli* (*E. coli*)]] host cells are free of association with any mammalian proteins. Depending upon the host employed, polypeptide of the invention is glycosylated with mammalian or other eukaryotic carbohydrates or is non-glycosylated. Polypeptides of the invention may also include an initial methionine amino acid residue (at position −1).

In addition to the recombinant versions of naturally-occurring allelic forms of canine G-CSF, the present invention also embraces other G-CSF products such as polypeptide analogs of canine G-CSF and fragments of canine G-CSF. All such forms of canine G-CSF may be useful in the method for treating or preventing infections in canine or feline animals. Following the procedures of the published application by Alton, et al. (WO/83/04053), hereby incorporated by reference, one can readily design and manufacture genes coding for microbial expression of polypeptides having primary conformations which differ from that herein specified for, in terms of the identity or location of one or more residues (e.g., substitutions, terminal and intermediate additions and deletions). Alternately, modifications of genomic and cDNA genes are readily accomplished by well-known site-directed mutagenesis techniques which generate analogs and derivatives of canine G-CSF. Such products share the hematopoietic biological properties of canine G-CSF. As examples, products of the invention include those which are foreshortened (e.g., by deletions); or those which are more stable to hydrolysis (and, therefore, have more pronounced or longer lasting effects than naturally-occurring); or which have been altered to delete one (or more) potential site(s) for n-linked or o-linked glycosylation (which result in higher activities for yeast-produced products); or which have one or more cysteine residues deleted or replaced (for example, by alanine or serine residues) and are more easily isolated in active form from microbial systems; or which have one or more tyrosine residues replaced by phenylalanine and bind more or less readily to G-CSF receptors on target cells. Also comprehended are polypeptide fragments duplicating only part of the continuous amino acid sequence or secondary conformations of canine G-CSF.

According to another aspect of the present invention, the DNA sequence described herein which encodes G-CSF polypeptides is valuable for the information which it provides concerning the amino acid sequence of this canine protein (and similar mammalian proteins) which has heretofore been unavailable. The DNA sequences are also valuable as products useful in effecting the large scale microbial synthesis of G-CSF having the same amino acid sequence as canine G-CSF, by a variety of recombinant techniques. Put another way, DNA sequences provided by the invention are useful in generating new and useful viral and plasmid DNA vectors, new and useful transformed and transfected prokaryotic and eukaryotic host cells (including bacterial, yeast, and mammalian cells grown in culture), and new and useful methods for cultured growth of such microbial host cells capable of expression of G-CSF having the canine amino acid sequence, variants or analogs. DNA sequences of the invention are also suitable materials for use as labelled probes in isolating canine G-CSF and related protein encoding cDNA and genomic DNA sequences of other mammalian species. DNA sequences are also useful in various alternative methods of protein synthesis (e.g., in insect cells) or in genetic therapy in mammals. DNA sequences of the invention are useful in developing transgenic mammalian species which may serve as eukaryotic "hosts" for production of G-CSF and G-CSF products in quantity. (See generally Palmiter, et al., *Science,* 22(4625), 809–814 (1983)).

Of applicability to canine G-CSF fragments and polypeptide analogs of the invention are reports of the immunological activity of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones, and the like. Included among the immune reactions of such polypeptides is the provocation of the formation of specific antibodies in immunologically active animals. (See, e.g., Lerner, et al., *Cell*, 23:309–310 (1981); Ross, et al., *Nature*, 294:654–656 (1981); Walter, et al., *Proc. Natl. Acad. Sci. (USA)*, 77:5197–5200 (1980); Lerner, et al., *Proc. Natl. Acad. Sci. (USA)*, 78:4882–4886 (1981); Wong, et al., *Proc. Natl. Acad. Sci. (USA)*, 78:7412–7416 (1981); Green, et al., *Cell*, 28:477–587 (1982); Nigg, et al., *Proc. Natl. Acad. Sci. (USA)*, 79:5322–5326 (1982); Baron, et al, *Cell*, 28:395–404 (1982); Dreesman, et al., *Nature*, 295:183–190 (1982); and Lerner, *Scientific American*, 248 (2):66–74 (1983)). See, also, Kaiser, et al. *Science*, 223:249–255 (1984) relating to biological and immunological activities of synthetic peptides which approximately share secondary structures of peptide hormones but may not share their primary structural conformation.

All of the above mentioned forms, fragments, variants and analogs of canine G-CSF may be useful in the method of treating or preventing infections in canine or feline animals as described herein.

In another embodiment of the invention, one or more additional colony stimulating factors are administered to the infected animal with G-CSF, egs. GM-CSF, M-CSF, multi-CSF (IL-3). The CSFs are administered together or separately. In a further embodiment, animal infections are treated by administering G-CSF with one or more of: the interferons (advantageously α-interferon), IL-2, IL-6 and TNF or with a traditional antibiotic.

This application also describes pharmaceutical compositions of G-CSF having the canine amino acid sequence in a pharmaceutically acceptable carrier. These compositions may be administered intravascularly, intraperitoneally, subcutaneously, intramuscularly, or by infusion using forms known to the pharmaceutical art. For intravascular, intraperitoneal, subcutaneous, or intramuscular administration, active drug components may be combined with a suitable carrier such as water, saline, aqueous dextrose, and the like. Regardless of the route of administration selected, the compositions of the present invention are formulated into pharmaceutically acceptable dosage forms by conventional methods known to those skilled in the art. An advantageous formulation is disclosed in commonly owned Ser. No. 285,159, hereby incorporated by reference. In one embodiment, sustained release formulations are used.

In one embodiment of the invention, G-CSF treatment is used in a prophylactic manner. For example, dogs or cats are treated prior to occurrences which may debilitate them, in order to boost and prime their capacity to fight off infections. Administration of the G-CSF can be made at the time the dogs or cats undergo surgery or radiation, etc.

Several variables will be taken into account by the ordinary artisan in determining the concentration of G-CSF in the therapeutic formulations and dosages to be administered. Variables include administration route and condition of the animal.

The following examples are presented by way of illustration of the invention and are specifically directed to procedures carried out prior to identification of canine G-CSF genomic and cDNA clones, to procedures resulting in such identification, and to the sequencing, development of expression systems based on genomic, cDNA and manufactured (or synthetic) genes and verification of expression of G-CSF having the canine amino acid sequence, and analog products in such systems. The method of isolating the canine G-CSF gene described below can also be used to isolate other animal G-CSF genes, which in turn can be used in producing other animal G-CSFs. In addition, the examples illustrate methods for treating or preventing infections in canine animals, comprising administering an effective amount of G-CSF.

EXAMPLE 1

Screening a Genomic Library for the Canine G-CSF Gene

In this example, oligonucleotide probes were used to screen for a genomic clone containing a canine G-CSF gene. A phage (EMBL-3) canine genomic library was obtained from Clontech, plated out on *E. coli* strain NM538, and screened using $^{32}$P phosphorylated oligonucleotide probes of the following sequences:

1. TCC CTG CCC CAG AGC TTC CTG CTC AAG TGC TTA GAG CAA GTG AGG AAG ATC CAG, and

2. GCC ATG CCG GCC TTC ACT TCT GCC TTC CAG CGC CGG GCA GGA GGG GTC CTG

A total of approximately $1.0 \times 10^6$ phage were plated on 8 22 cm square petri dishes and plaque lifted in duplicate onto Gene Screen Plus transfer hybridization membranes. One set of membranes was hybridized to probe 1 and the other set was hybridizated to probe 2 using the procedures described in Maniatis et al., *Molecular Cloning, A Laboratory Manual* (Cold Spring Harbor Laboratory, New York, 1982). Hybridizations were done at 55° C. overnight in 6×SSC, 5× Denhardts, 50 µg/ml sheared herring sperm DNA. A total of 1 positive clone was observed which hybridized to both probes. This clone was rescreened until an isolated plaque was obtained and was grown in a 3 liter culture and phage DNA was prepared as described in Maniatus, supra. This DNA was mapped by restriction enzyme digestion and Southern blotting using the radiolabeled probes. The mapping results showed that a Asp718 fragment of about 3700 bases contained the entire G-CSF region. DNA was digested with Asp718 to release an approximately 3700 bp canine G-CSF containing fragment which was subsequently subcloned into pUC19 at the Asp 718 site and further mapped by restriction endonuclease digests and Southern blotting.

A restriction endonuclease map (approximately 3.7 kb) of genomic DNA containing the canine G-CSF gene is shown in FIG. 1. The sequence for the entire coding region of the mature canine G-CSF was determined by subcloning fragments into M13 and sequencing them by the dideoxy method described in Sanger et al., *Proc. Natl. Acad. Sci. U.S.A.* 74, 5463–5467 (1977). Sequences were confirmed or extended by utilizing internal primers off of the same clones. The sequence for the coding region was deduced by direct comparison with the human genomic G-CSF sequence (FIG. 3) and is shown in FIG. 2. Splice juncture sites and amino terminal processing of the protein were assumed to occur at the same places as the human G-CSF. The DNA sequence codes for a mature protein of the same length as the human G-CSF (174 amino acids) and the proteins are 81% homologous (see FIG. 7).

EXAMPLE 2

Construction of Synthetic Canine G-CSF Genes and Expression of Such G-CSF Genes This example relates to preparation of manufactured genes encoding canine G-CSF and including *E. coli* preference codons, and to expression of such G-CSF.

Synthetic genes were designed to allow for the expression of canine granulocyte colony stimulating factor in *E. coli* [cG-CSF dna3 (FIGS. 4–6)]. Canine G-CSF is 174 amino acids in length and is 81% homologus to the human form of G-CSF (174 a.a.).

The gene cG-CSF dna3 (FIGS. 4–6) was designed with maximum bias for *E. coli* codon preference. For gene cG-CSF dna3, in addition to the coding sequence, an initiation ATG, leader and terminator sequences and 5' Xba1 and 3' BamH1 restriction sites were entered. The gene, cG-CSF dna3, was also designed to have minimum secondary interactions and sufficient unique restriction sites for subunit assembly and gene manipulation. BamH1 and Pst1 sites were incorporated at positions identical to those found in the human G-CSF gene noted in commonly owned U.S. Pat. No. 4,810,643. This allows for generation of unique human/canine hybrid genes and their protein products.

The gene was designed as two subunits (Subunit I (Xba1-HindIII), and Subunit II (HindIII-BamH1) for cloning into sequencing/expression vectors (FIG. 6). Subunit I contains a short leader sequence with an Xba1 cloning end and the ribosome binding site (RBS). Subunit II contains a pair of redundant stop codons and the BamH1 cloning end.

Briefly stated, the protocol employed was generally as set out in the disclosure of co-owned Alton, et al., PCT Publication No. WO83/04053, which is incorporated by reference herein. The gene was designed for initial assembly of component oligonucleotides into multiple duplexes which, in turn, were assembled into two discrete sections (FIG. 6). These sections were designed for ready amplification and, upon removal from the amplification system, could be assembled sequentially or through a multiple fragment ligation into a suitable expression vector.

The construction of Sections I and II is illustrated in FIGS. 5 and 6. In the construction of Section I, as shown in FIGS. 5 and 6, 16 oligonucleotides were assembled into 8 duplexes. The 8 duplexes were then ligated to form Section I. It may also be noted in FIG. 6 that Section I includes an upstream Xba1 sticky end and a downstream HindIII sticky end useful for ligation to amplification and expression vectors and for ligation to Section II.

Section II was constructed as shown in FIGS. 5 and 6. For this construction, 16 oligonucleotides were assembled into 8 duplexes. The 8 duplexes were then ligated to form Section II as depicted in FIG. 6. As also shown in FIG. 6, Section II includes an upstream HindIII sticky end and a downstream BamH1 sticky end useful for ligating into amplification and expression vectors, and to Section I.

Although any suitable vector may be employed to express this DNA, the expression plasmid pCFM536 may readily be used. This plasmid is described in U.S. Pat. No. 4,710,473 hereby incorporated by reference. Control of expression in the pCFM536 plasmid is by means of a lambda pL promoter, which itself may be under the control of a CI857 repressor gene (such as is provided in *E. coli* strain FM5 (ATCC deposit 53911).

Section I was initially cloned into M13 from Xba1 to HindIII and sequenced by the dideoxy method (Sanger supra). Section II was cloned into M13 from HindIII to EcoR1 and was also sequenced by the dideoxy method. Section I was cut out of M13 from Xba1 to HindIII and Section II was cut out of M13 from HindIII to EcoR1. These two fragments were then ligated with pCFM536 cut from Xba1 to BamH1 and transformed into *E. coli* strain FM5 to generate pCFM536cG-CSF.

This plasmid contains the λpL promoter/operator region and has a temperature sensitive replicon. When *E. coli* strain FM5 harboring pCFM536cG-CSF is cultured at 28° C., the plasmid copy number is maintained at 10–20 copies/cell, and transcription from the λpL promoter is regulated by a temperature sensitive repressor. Growth at 42° C. results in an increased copy number and release of repression at the λpL promoter. Recombinant G-CSF having the canine sequence begins to accumulate at elevated temperatures as the result of promoter activation and plasmid amplification. The λpL promoter lies just upstream from the ribosome binding site and the methionine initiation codon of canine G-CSF. The transcription terminator, t-oop, lies just downstream from the two translational stop codons near the 3' end of the gene. Strain FM5 harboring the plasmid, pCFM536cG-CSF, expresses recombinant G-CSF having the canine sequence at up to 30% of the total cellular protein.

EXAMPLE 3

Construction of Canine G-CSF Analogs

This example relates to the use of recombinant methods to generate an analog of canine G-CSF wherein the cysteine at position 17 was individually replaced by a serine.

Site directed mutagenesis procedures according to Souza, et al., published PCT Application No. WO85/00817, published Feb. 28, 1985, hereby incorporated by reference, were carried out using the oligonucleotide CTG CTG AAA TCC CTC GAG CAG.

EXAMPLE 4

*E. coli* Canine G-CSF Purification

The general purification method is disclosed in commonly owned Ser. No. 348,011 hereby incorporated by reference.

Cell Breakage and Sarkosyl Solubilization and Oxidation

About 200 grams of cell paste were weighed out in 1.5 liters of cold water. The cell paste was dispersed with a homogenizer until completely dispersed. The homogenate was then passed through a Gaulin Homogenizer four times at 8000 psig. The material was then centrifuged in the Beckman J2 21 centrifuge using the JA 10 rotor at 9000 rpm for 30 minutes at 4° C. The supernatant was decanted and discarded. The pellet was resuspended in 1.5 liters of cold water and again centrifuged in the Beckman J2 21 centrifuge using the JA 10 rotor at 9000 rpm for 30 minutes at 4° C. The supernatant was decanted and discarded. The pellet was resuspended in 760 mL water and 40 mL 1M Tris, pH 8.0 was added followed by 200 mL 10% Sarkosyl. After this material stirred at room temperature for about ten minutes, 1 mL 1% copper sulfate pentahydrate was added. This material was stirred at room temperature overnight (approximately 16 hours). The material was then centrifuged in the Beckman J2 21 centrifuge using the JA 10 rotor at 9000 rpm for 30 minutes at 4° C. The supernatant was decanted and saved. The pellets were discarded.

Dowex Removal of Sarkosyl

To the supernatant was added 1 liter of cold water and then 2 liters cold 20 mM Tris, pH 8.0 and then 800 grams prepared Dowex (see Ser. No. 348,011 hereby incorporated by reference) was added. This slurry was stirred at 4° C. for 90 minutes. The slurry was poured through a column and the flow through collected. The resin was washed with 800 mL cold 20 mM Tris, pH 8.0 which was added to the flow through giving 4800 mL.

DE52 Cellulose Ion Exchange Chromatography

About 4800 mL of material was loaded directly onto a 200 mL DE52 cellulose ion exchange column equilibrated in 20 mM Tris, pH 8.0. The product was eluted off of the column using 100 mM NaCl in 20 mM Tris, pH 9.0. About 1270 mL was collected at approximately 0.8 mg/mL, giving approximately 1 gram.

CM-Sepharose Fast Flow Chromatography

The DE52 100 mM NaCl material was concentrated using a Pellicon system (with a 10,000 MW membrane) to approximately 200 mL. The material was adjusted to pH 5.4 using 50% acetic acid. Six volumes of cold water were added and the material was then loaded directly onto a 50 mL CM-Sepharose Fast Flow ion exchange column equilibrated in 20 mM sodium acetate, pH 5.4. The product was eluted off of the column using a 1 liter gradient from 0–0.2M NaCl in 20 mM sodium acetate, pH 5.4. About 100 10 mL fractions were collected. Based on the chromatogram results the fractions of interest were analyzed on a 15% SDS gel. Based on the gel results, fractions 30–51 were pooled giving 258 mL at approximately 2.6 mg/mL, or 685 mgs.

Diafiltration

The CM pool was adjusted to pH 3.5 using 0.1N HCL and then diafiltered using a Pellicon with a 10,000 MW membrane vs. 0.35 mM HCl-Water. The final volume was adjusted to 685 mL to give material at a final concentration of 1 mg/mL.

EXAMPLE 5

In vivo Activity of Canine G-CSF

Two young adult, healthy mixed breed dogs (one 25 kg male, one 28.6 kg female) were used for this study. The dogs were acclimated to the hospital environment for one week prior to the onset of the study. Complete blood and platelet counts were done three days prior and then immediately prior to the first injection of recombinant cG-CSF. Recombinant *E. coli* G-CSF having the amino acid sequence of canine G-CSF was diluted in sterile water to 100 ug/ml and placed in multiple dose vials. The G-CSF was maintained at 4° C.

A dosage of 5 ug/kg/day was administered subcutaneously to each dog for 4 weeks at the same time each day. Blood for a CBC and platelet count was drawn immediately prior to each G-CSF injection and submitted to the clinical pathology laboratory for evaluation. Daily blood counts were performed until three consecutive daily counts remained stable. Blood was then drawn every other day for two weeks, then every third day the final week.

After 28 days, G-CSF administration was discontinued. Blood counts were followed every other day to determine how rapidly they returned to normal. Once within normal range, G-CSF was started again at the same dosage and administered for another five days to determine the leukocyte response.

Figure 8:
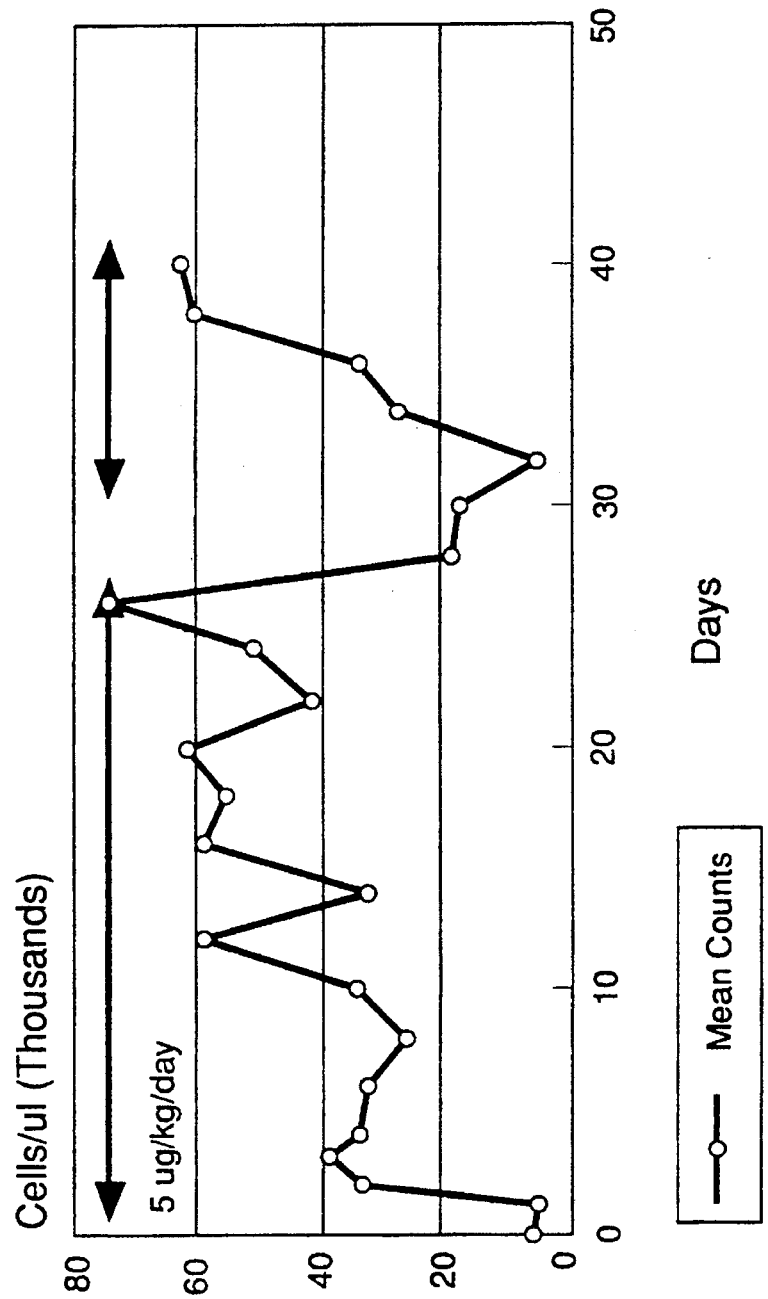
FIGS. 8–9 are graphic representations of the results obtained in Example 5 which relates to treatment of dogs with G-CSF having the canine amino acid sequence.
Figure 9:
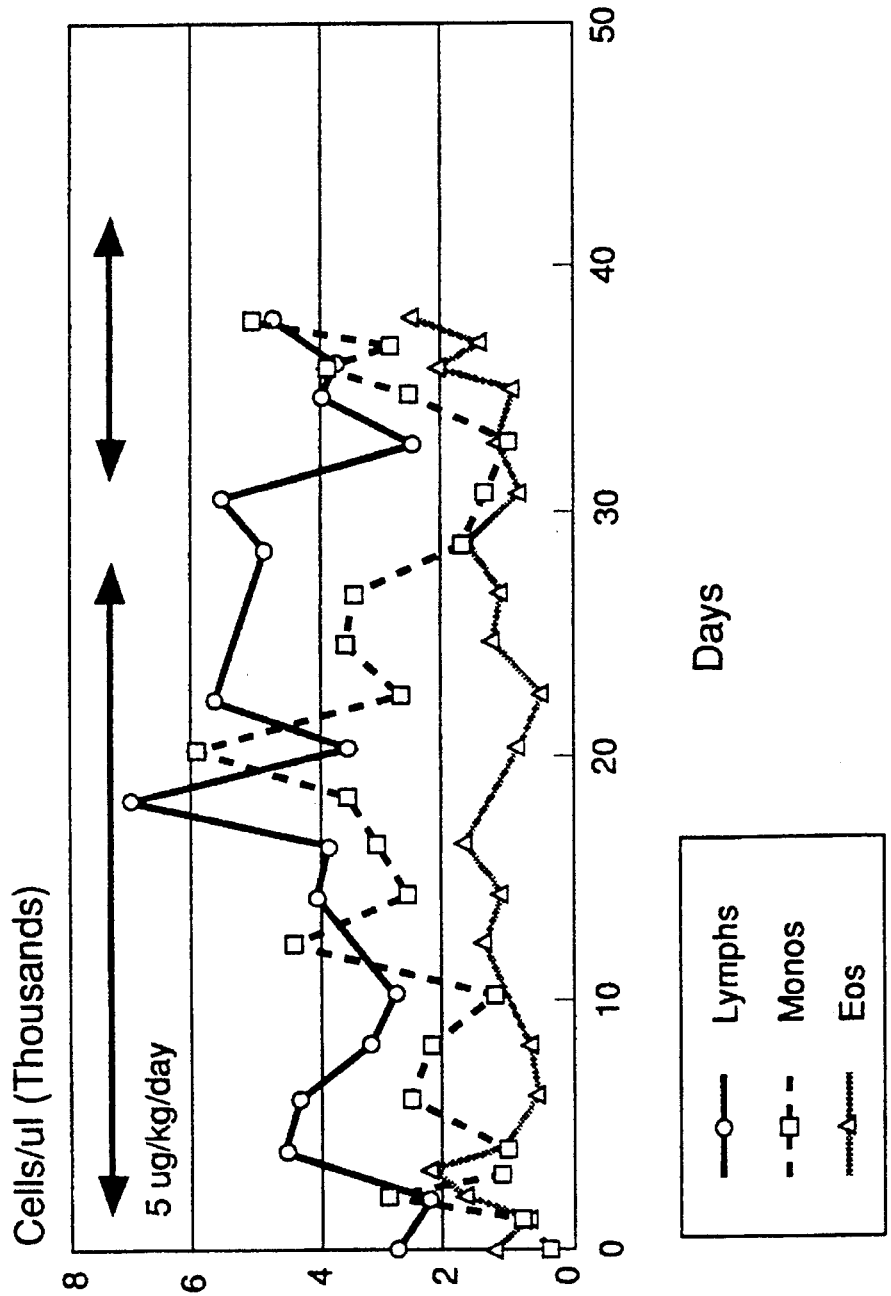

Physical examinations were performed on a daily basis. Karnofsky's performance scores were assigned daily to both animals. Body weights and body temperatures were recorded daily. In addition, toxicity evaluation was performed daily. The mean white blood cell count prior to administration of G-CSF was 8,650/ul (neutrophils: 4,880/ul; lymphocytes: 2,398/ul; monocytes: 667/ul; eosinophils: 704/ul; and platelets: 297,000/ul). Twenty-four hours following the first injection of G-CSF, the mean white blood cell count was 39,150/ul (neutrophils: 31,257/ul; neutrophilic bands: 391/ul; lymphocytes: 2,803/ul; monocytes: 2,951/ul; eosinophils: 1,747/ul; platelets: 322,500/ul). This represents a 4.5 fold increase in total white blood cell count within 24 hours. Neutrophils increased by a factor of 6.4 (see FIG. 8). Monocytes rose by a factor of 4.4 (see FIG. 9). Although the dosage of G-CSF remained at 5 ug/kg/day, an additional increase in blood counts was noted on day eleven. Mean white blood cell count on day nine was 32,550/ul (mean neutrophil count: 26,682/ul). On day eleven, the mean white blood cell count was 69,200/ul (mean neutrophil count: 58,764/ul) representing an additional two-fold increase from day nine to day eleven and an eight-fold increase from day one (prior to G-CSF administration). Blood counts remained elevated throughout the 28 day period of administration of G-CSF in one dog. In the second dog there were 3 days on which decreases in the leukocyte counts were evident 24 hours after administration of a reduced dosage. Counts returned to their pretreatment levels by the fifth day after G-CSF was stopped. Upon resumption of G-CSF administration, the mean white blood cell count increased by a factor of 6.3 (from mean of 9,450/ul to mean of 59,500/ul). These elevated counts persisted until G-CSF administration was discontinued five days later (See FIGS. 8 and 9).

Recombinant G-CSF having the amino acid sequence of canine G-CSF increased leukocyte counts (primarily neutrophils) and leukocyte counts were maintained at elevated levels as long as administration of the G-CSF was continued. Initial increases in leukocyte counts were most likely due to demargination of blood cells. The decrease in leukocyte counts observed following a reduced G-CSF dosage followed by a rapid return to elevated leukocyte levels with a full dosage demonstrate a rapid, dose-dependent response. There was no development of neutralizing antibodies to the G-CSF.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A polypeptide product of expression of a DNA molecule set forth in FIGS. 2A–2B (SEQ ID NO. 1), said polypeptide product being free from association with protein of canine origin.

2. A polypeptide product of claim 1 wherein such DNA is expressed in a procaryote.

3. A polypeptide product of claim 1 wherein such DNA is expressed in a eukaryote.

4. A pharmaceutical composition comprising the polypeptide of any of claims 1, 2, or 3 and a carrier.

* * * * *

UNITED STATES PATENT AND TRADEMARK OFFICE
CERTIFICATE OF CORRECTION

PATENT NO. : 5,606,024

DATED : February 25, 1997

INVENTOR(S) : Thomas C. Boone, Allan L. Miller

It is certified that error appears in the above-identified patent and that said Letters Patent is hereby corrected as shown below:

Column 3, line 64; change "3" to --3A-3C--

Signed and Sealed this

Second Day of June, 1998

Attest:

BRUCE LEHMAN

*Attesting Officer*        *Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:

( A ) LENGTH: 522 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..522

( x i ) SEQUENCE DESCRIPTION: SEQ ID NO:1:

| GCC | CCC | CTG | GGC | CCT | ACC | GGC | CCC | CTG | CCC | CAG | AGC | TTC | CTG | CTC | AAG | 48 |
|---|---|---|---|---|---|---|---|---|---|---|---|---|---|---|---|---|
| Ala | Pro | Leu | Gly | Pro | Thr | Gly | Pro | Leu | Pro | Gln | Ser | Phe | Leu | Leu | Lys | |
| 1 | | | | 5 | | | | | 10 | | | | | 15 | | |

| TGC | CTA | GAG | CAA | ATG | AGG | AAG | GTC | CAG | GCT | GAT | GGC | ACG | GCG | CTG | CAG | 96 |
|---|---|---|---|---|---|---|---|---|---|---|---|---|---|---|---|---|
| Cys | Leu | Glu | Gln | Met | Arg | Lys | Val | Gln | Ala | Asp | Gly | Thr | Ala | Leu | Gln | |
| | | | 20 | | | | | 25 | | | | | 30 | | | |

| GAG | ACG | CTG | TGT | GCC | ACC | CAC | CAG | CTG | TGC | CAT | CCT | GAG | GAG | TTG | GTG | 144 |
|---|---|---|---|---|---|---|---|---|---|---|---|---|---|---|---|---|
| Glu | Thr | Leu | Cys | Ala | Thr | His | Gln | Leu | Cys | His | Pro | Glu | Glu | Leu | Val | |
| | | 35 | | | | | 40 | | | | | 45 | | | | |

| CTG | CTC | GGG | CAC | GCT | CTG | GGC | ATC | CCC | CAG | CCT | CCC | CTG | AGC | AGC | TGC | 192 |
|---|---|---|---|---|---|---|---|---|---|---|---|---|---|---|---|---|
| Leu | Leu | Gly | His | Ala | Leu | Gly | Ile | Pro | Gln | Pro | Pro | Leu | Ser | Ser | Cys | |
| | 50 | | | | | 55 | | | | | 60 | | | | | |

| TCC | AGC | CAG | GCC | CTG | CAG | CTG | ATG | GGC | TGC | CTG | CGT | CAA | CTC | CAC | AGC | 240 |
|---|---|---|---|---|---|---|---|---|---|---|---|---|---|---|---|---|
| Ser | Ser | Gln | Ala | Leu | Gln | Leu | Met | Gly | Cys | Leu | Arg | Gln | Leu | His | Ser | |
| 65 | | | | | 70 | | | | | 75 | | | | | 80 | |

| GGC | CTC | TTC | CTC | TAC | CAG | GGC | CTC | CTG | CAG | GCC | CTG | GCA | GGG | ATA | TCC | 288 |
|---|---|---|---|---|---|---|---|---|---|---|---|---|---|---|---|---|
| Gly | Leu | Phe | Leu | Tyr | Gln | Gly | Leu | Leu | Gln | Ala | Leu | Ala | Gly | Ile | Ser | |
| | | | | 85 | | | | | 90 | | | | | 95 | | |

| CCC | GAG | TTA | GCG | CCC | ACC | TTG | GAC | ACA | CTG | CAG | CTG | GAC | ACC | ACC | GAC | 336 |
|---|---|---|---|---|---|---|---|---|---|---|---|---|---|---|---|---|
| Pro | Glu | Leu | Ala | Pro | Thr | Leu | Asp | Thr | Leu | Gln | Leu | Asp | Thr | Thr | Asp | |
| | | | 100 | | | | | 105 | | | | | 110 | | | |

| TTT | GCC | ATC | AAC | ATC | TGG | CAG | CAG | ATG | GAA | GAT | CTA | GGA | ATG | GCC | CCC | 384 |
|---|---|---|---|---|---|---|---|---|---|---|---|---|---|---|---|---|
| Phe | Ala | Ile | Asn | Ile | Trp | Gln | Gln | Met | Glu | Asp | Leu | Gly | Met | Ala | Pro | |
| | | 115 | | | | | 120 | | | | | 125 | | | | |

| GCC | GTG | CCA | CCT | ACC | CAG | GGC | ACC | ATG | CCA | GCC | TTC | ACC | TCG | GCC | TTC | 432 |
|---|---|---|---|---|---|---|---|---|---|---|---|---|---|---|---|---|
| Ala | Val | Pro | Pro | Thr | Gln | Gly | Thr | Met | Pro | Ala | Phe | Thr | Ser | Ala | Phe | |
| | 130 | | | | | 135 | | | | | 140 | | | | | |

| CAG | CGC | CGG | GCA | GGA | GGT | GTC | CTG | GTG | GCC | TCC | AAC | CTG | CAG | AGC | TTC | 480 |
|---|---|---|---|---|---|---|---|---|---|---|---|---|---|---|---|---|
| Gln | Arg | Arg | Ala | Gly | Gly | Val | Leu | Val | Ala | Ser | Asn | Leu | Gln | Ser | Phe | |
| 145 | | | | | 150 | | | | | 155 | | | | | 160 | |

| CTG | GAG | CTG | GCA | TAT | CGC | GCT | CTG | CGC | CAC | TTT | GCC | AAA | CCC | | | 522 |
|---|---|---|---|---|---|---|---|---|---|---|---|---|---|---|---|---|
| Leu | Glu | Leu | Ala | Tyr | Arg | Ala | Leu | Arg | His | Phe | Ala | Lys | Pro | | | |
| | | | 165 | | | | | 170 | | | | | | | | |

( 2 ) INFORMATION FOR SEQ ID NO:2:

( i ) SEQUENCE CHARACTERISTICS:
( A ) LENGTH: 174 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Ala | Pro | Leu | Gly | Pro | Thr | Gly | Pro | Leu | Pro | Gln | Ser | Phe | Leu | Leu | Lys |
|---|---|---|---|---|---|---|---|---|---|---|---|---|---|---|---|
| 1 | | | | 5 | | | | | 10 | | | | | 15 | |

| Cys | Leu | Glu | Gln | Met | Arg | Lys | Val | Gln | Ala | Asp | Gly | Thr | Ala | Leu | Gln |
|---|---|---|---|---|---|---|---|---|---|---|---|---|---|---|---|
| | | | 20 | | | | | 25 | | | | | 30 | | |

| Glu | Thr | Leu | Cys | Ala | Thr | His | Gln | Leu | Cys | His | Pro | Glu | Glu | Leu | Val |
|---|---|---|---|---|---|---|---|---|---|---|---|---|---|---|---|
| | | 35 | | | | | 40 | | | | | 45 | | | |

| Leu | Leu | Gly | His | Ala | Leu | Gly | Ile | Pro | Gln | Pro | Pro | Leu | Ser | Ser | Cys |
|---|---|---|---|---|---|---|---|---|---|---|---|---|---|---|---|
| | 50 | | | | | 55 | | | | | 60 | | | | |

| | | | | | | | | | | | | | | | |
|---|---|---|---|---|---|---|---|---|---|---|---|---|---|---|---|
|Ser|Ser|Gln|Ala|Leu|Gln|Leu|Met|Gly|Cys|Leu|Arg|Gln|Leu|His|Ser|
|65| | | |70| | | |75| | | | | | |80|
|Gly|Leu|Phe|Leu|Tyr|Gln|Gly|Leu|Leu|Gln|Ala|Leu|Ala|Gly|Ile|Ser|
| | | | |85| | | |90| | | | |95| | |
|Pro|Glu|Leu|Ala|Pro|Thr|Leu|Asp|Thr|Leu|Gln|Leu|Asp|Thr|Thr|Asp|
| | | |100| | | |105| | | | |110| | | |
|Phe|Ala|Ile|Asn|Ile|Trp|Gln|Gln|Met|Glu|Asp|Leu|Gly|Met|Ala|Pro|
| | | |115| | | |120| | | | |125| | | |
|Ala|Val|Pro|Pro|Thr|Gln|Gly|Thr|Met|Pro|Ala|Phe|Thr|Ser|Ala|Phe|
| | |130| | | |135| | | | |140| | | | |
|Gln|Arg|Arg|Ala|Gly|Gly|Val|Leu|Val|Ala|Ser|Asn|Leu|Gln|Ser|Phe|
|145| | | | |150| | | |155| | | | |160| |
|Leu|Glu|Leu|Ala|Tyr|Arg|Ala|Leu|Arg|His|Phe|Ala|Lys|Pro| | |
| | | | |165| | | |170| | | | | | | |

( 2 ) INFORMATION FOR SEQ ID NO:3:

( i ) SEQUENCE CHARACTERISTICS:
        ( A ) LENGTH: 3070 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GGGGACAGGC  TTGAGAATCC  CAAAGGAGAG  GGGCAAAGGA  CACTGCCCCC  GCAAGTCTGC     60
CAGAGCAGAG  AGGGAGACCC  CGACTCAGCT  GCCACTTCCC  CACAGGCTCG  TGCCGCTTCC    120
AGGCGTCTAT  CAGCGGCTCA  GCCTTTGTTC  AGCTGTTCTG  TTCAAACACT  CTGGGGCCAT    180
TCAGGCCTGG  GTGGGGCAGC  GGGAGGAAGG  GAGTTTGAGG  GGGGCAAGGC  GACGTCAAAG    240
GAGGATCAGA  GATTCCACAA  TTTCACAAAA  CTTTCGCAAA  CAGCTTTTTG  TTCCAACCCC    300
CCTGCATTGT  CTTGGACACC  AAATTTGCAT  AAATCCTGGG  AAGTTATTAC  TAAGCCTTAG    360
TCGTGGCCCC  AGGTAATTTC  CTCCCAGGCC  TCCATGGGGT  TATGTATAAA  GGGCCCCCTA    420
GAGCTGGGCC  CCAAAACAGC  CCGGAGCCTG  CAGCCCAGCC  CCACCCAGAC  CCATGGCTGG    480
ACCTGCCACC  CAGAGCCCCA  TGAAGCTGAT  GGGTGAGTGT  CTTGGCCCAG  GATGGGAGAG    540
CCGCCTGCCC  TGGCATGGGA  GGGAGGCTGG  TGTGACAGAG  GGGCTGGGGA  TCCCCGTTCT    600
GGGAATGGGG  ATTAAAGGCA  CCCAGTGTCC  CCGAGAGGGC  CTCAGGTGGT  AGGGAACAGC    660
ATGTCTCCTG  AGCCCGCTCT  GTCCCCAGCC  CTGCAGCTGC  TGCTGTGGCA  CAGTGCACTC    720
TGGACAGTGC  AGGAAGCCAC  CCCCCTGGGC  CCTGCCAGCT  CCCTGCCCCA  GAGCTTCCTG    780
CTCAAGTGCT  TAGAGCAAGT  GAGGAAGATC  CAGGGCGATG  GCGCAGCGCT  CCAGGAGAAG    840
CTGGTGAGTG  AGGTGGGTGA  GAGGGCTGTG  GAGGGAAGCC  CGGTGGGGAG  AGCTAAGGGG    900
GATGGAACTG  CAGGGCCAAC  ATCCTCTGGA  AGGGACATGG  GAGAATATTA  GGAGCAGTGG    960
AGCTGGGGAA  GGCTGGGAAG  GGACTTGGGG  AGGAGGACCT  TGGTGGGGAC  AGTGCTCGGG   1020
AGGGCTGGCT  GGGATGGGAG  TGGAGGCATC  ACATTCAGGA  GAAAGGGCAA  GGGCCCCTGT   1080
GAGATCAGAG  AGTGGGGGTG  CAGGGCAGAG  AGGAACTGAA  CAGCCTGGCA  GGACATGGAG   1140
GGAGGGGAAA  GACCAGAGAG  TCGGGGAGGA  CCCGGGAAGG  AGCGGCGACC  CGGCCACGGC   1200
GAGTCTCACT  CAGCATCCTT  CCATCCCCAG  TGTGCCACCT  ACAAGCTGTG  CCACCCCGAG   1260
GAGCTGGTGC  TGCTCGGACA  CTCTCTGGGC  ATCCCCTGGG  CTCCCCTGAG  CAGCTGCCCC   1320
AGCCAGGCCC  TGCAGCTGGT  GAGTGTCAGG  AAAGGATAAG  GCTAATGAGG  AGGGGGAAGG   1380
```

-continued

| | | | | | | |
|---|---|---|---|---|---|---|
| AGAGGAGGAA | CACCCATGGG | CTCCCCCATG | TCTCCAGGTT | CCAAGCTGGG | GGCCTGACGT | 1440 |
| ATCTCAGGCA | GCACCCCCTA | ACTCTTCCGC | TCTGTCTCAC | AGGCAGGCTG | CTTGAGCCAA | 1500 |
| CTCCATAGCG | GCCTTTTCCT | CTACCAGGGG | CTCCTGCAGG | CCCTGGAAGG | GATCTCCCCC | 1560 |
| GAGTTGGGTC | CCACCTTGGA | CACACTGCAG | CTGGACGTCG | CCGACTTTGC | CACCACCATC | 1620 |
| TGGCAGCAGG | TGAGCCTTGT | TGGGCAGGGT | GGCCAAGGTC | GTGCTGGCAT | CTGGGCACC | 1680 |
| ACAGCCGGGC | CTGTGTATGG | GCCCTGTCCA | TGCTGTCAGC | CCCCAGCATT | TCCTCATTTG | 1740 |
| TAATAACGCC | CACTCAGAAG | GGCCCAACCA | CTGATCACAG | CTTTCCCCCA | CAGATGGAAG | 1800 |
| AACTGGGAAT | GGCCCCTGCC | CTGCAGCCCA | CCCAGGGTGC | CATGCCGGCC | TTCGCCTCTG | 1860 |
| CTTTCCAGCG | CCGGGCAGGA | GGGGTCCTGG | TTGCCTCCCA | TCTGCAGAGC | TTCCTGGAGG | 1920 |
| TGTCGTACCG | CGTTCTACGC | CACCTTGCCC | AGCCCTGAGC | CAAGCCCTCC | CCATCCCATG | 1980 |
| TATTTATCTC | TATTTAATAT | TTATGTCTAT | TTAAGCCTCA | TATTTAAAGA | CAGGGAAGAG | 2040 |
| CAGAACGGAG | CCCCAGGCCT | CTGTGTCCTT | CCCTGCATTT | CTGAGTTTCA | TTCTCCTGCC | 2100 |
| TGTAGCAGTG | AGAAAAAGCT | CCTGTCCTCC | CATCCCCTGG | ACTGGGAGGT | AGATAGGTAA | 2160 |
| ATACCAAGTA | TTTATTACTA | TGACTGCTCC | CCAGCCCTGG | CTCTGCAATG | GGCACTGGGA | 2220 |
| TGAGCCGCTG | TGAGCCCCTG | GTCCTGAGGG | TCCCCACCTG | GGACCCTTGA | GAGTATCAGG | 2280 |
| TCTCCCACGT | GGGAGACAAG | AAATCCCTGT | TTAATATTTA | AACAGCAGTG | TTCCCCATCT | 2340 |
| GGGTCCTTGC | ACCCCTCACT | CTGGCCTCAG | CCGACTGCAC | AGCGGCCCCT | GCATCCCCTT | 2400 |
| GGCTGTGAGG | CCCCTGGACA | AGCAGAGGTG | GCCAGAGCTG | GGAGGCATGG | CCCTGGGGTC | 2460 |
| CCACGAATTT | GCTGGGGAAT | CTCGTTTTTC | TTCTTAAGAC | TTTTGGGACA | TGGTTTGACT | 2520 |
| CCCGAACATC | ACCGACGTGT | CTCCTGTTTT | TCTGGGTGGC | CTCGGACAC | CTGCCCTGCC | 2580 |
| CCCACGAGGG | TCAGGACTGT | GACTCTTTTT | AGGGCCAGGC | AGGTGCCTGG | ACATTTGCCT | 2640 |
| TGCTGGATGG | GGACTGGGGA | TGTGGGAGGG | AGCAGACAGG | AGGAATCATG | TCAGGCCTGT | 2700 |
| GTGTGAAAGG | AAGCTCCACT | GTCACCCTCC | ACCTCTTCAC | CCCCCACTCA | CCAGTGTCCC | 2760 |
| CTCCACTGTC | ACATTGTAAC | TGAACTTCAG | GATAATAAAG | TGTTTGCCTC | CAGTCACGTC | 2820 |
| CTTCCTCCTT | CTTGAGTCCA | GCTGGTGCCT | GGCCAGGGGC | TGGGGAGGTG | GCTGAAGGGT | 2880 |
| GGGAGAGGCC | AGAGGGAGGT | CGGGGAGGAG | GTCTGGGGAG | GAGGTCCAGG | GAGGAGGAGG | 2940 |
| AAAGTTCTCA | AGTTCGTCTG | ACATTCATTC | CGTTAGCACA | TATTTATCTG | AGCACCTACT | 3000 |
| CTGTGCAGAC | GCTGGGCTAA | GTGCTGGGGA | CACAGCAGGG | AACAAGGCAG | ACATGGAATC | 3060 |
| TGCACTCGAG | | | | | | 3070 |

( 2 ) INFORMATION FOR SEQ ID NO:4:

( i ) SEQUENCE CHARACTERISTICS:
        ( A ) LENGTH: 525 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS(B)
        ( B ) LOCATION: 1..525

( x i ) SEQUENCE DESCRIPTION: SEQ ID NO:4:

| ATG | GCA | CCT | TTA | GGT | CCA | ACT | GGT | CCT | CTG | CCT | CAA | AGT | TTC | CTG | CTG | 48 |
|---|---|---|---|---|---|---|---|---|---|---|---|---|---|---|---|---|
| Met | Ala | Pro | Leu | Gly | Pro | Thr | Gly | Pro | Leu | Pro | Gln | Ser | Phe | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AAA | TGC | CTC | GAG | CAG | ATG | CGT | AAA | GTT | CAA | GCT | GAT | GGT | ACC | GCA | CTC | 96 |
| Lys | Cys | Leu | Glu 20 | Gln | Met | Arg | Lys 25 | Val | Gln | Ala | Asp | Gly 30 | Thr | Ala | Leu | |
| CAA | GAA | ACT | CTG | TGC | GCA | ACT | CAC | CAA | CTG | TGC | CAC | CCT | GAA | GAA | CTC | 144 |
| Gln | Glu | Thr 35 | Leu | Cys | Ala | Thr | His 40 | Gln | Leu | Cys | His | Pro 45 | Glu | Glu | Leu | |
| GTA | CTG | CTC | GGT | CAC | GCA | CTC | GGT | ATT | CCG | CAG | CCG | CCG | CTG | TCT | TCT | 192 |
| Val | Leu 50 | Leu | Gly | His | Ala | Leu | Gly 55 | Ile | Pro | Gln | Pro 60 | Pro | Leu | Ser | Ser | |
| TGC | TCC | TCT | CAG | GCT | CTG | CAA | CTC | ATG | GGT | TGC | CTC | CGT | CAA | CTG | CAT | 240 |
| Cys 65 | Ser | Ser | Gln | Ala | Leu 70 | Gln | Leu | Met | Gly | Cys 75 | Leu | Arg | Gln | Leu | His 80 | |
| TCT | GGC | CTG | TTC | CTG | TAC | CAG | GGT | CTC | CTG | CAA | GCT | TTG | GCT | GGC | ATC | 288 |
| Ser | Gly | Leu | Phe | Leu 85 | Tyr | Gln | Gly | Leu | Leu 90 | Gln | Ala | Leu | Ala | Gly 95 | Ile | |
| TCT | CCG | GAA | CTC | GCA | CCT | ACT | CTC | GAC | ACT | CTG | CAG | CTC | GAC | ACT | ACC | 336 |
| Ser | Pro | Glu | Leu 100 | Ala | Pro | Thr | Leu | Asp 105 | Thr | Leu | Gln | Leu | Asp 110 | Thr | Thr | |
| GAC | TTC | GCT | ATC | AAC | ATT | TGG | CAG | CAA | ATG | GAA | GAT | CTG | GGC | ATG | GCA | 384 |
| Asp | Phe | Ala 115 | Ile | Asn | Ile | Trp | Gln 120 | Gln | Met | Glu | Asp | Leu 125 | Gly | Met | Ala | |
| CCG | GCT | GTT | CCG | CCG | ACT | CAG | GGC | ACT | ATG | CCT | GCT | TTT | ACT | TCT | GCT | 432 |
| Pro | Ala 130 | Val | Pro | Pro | Thr | Gln 135 | Gly | Thr | Met | Pro | Ala 140 | Phe | Thr | Ser | Ala | |
| TTC | CAG | CGT | CGT | GCT | GGT | GGT | GTA | CTC | GTA | GCT | TCT | AAC | CTC | CAG | TCT | 480 |
| Phe 145 | Gln | Arg | Arg | Ala | Gly 150 | Gly | Val | Leu | Val | Ala 155 | Ser | Asn | Leu | Gln | Ser 160 | |
| TTC | CTC | GAA | CTC | GCT | TAC | CGT | GCT | CTG | CGT | CAC | TTC | GCT | AAA | CCG | | 525 |
| Phe | Leu | Glu | Leu | Ala 165 | Tyr | Arg | Ala | Leu | Arg 170 | His | Phe | Ala | Lys | Pro 175 | | |

( 2 ) INFORMATION FOR SEQ ID NO:5:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | | |
|---|---|---|---|---|---|---|---|---|---|---|---|---|---|---|---|
| Met 1 | Ala | Pro | Leu | Gly 5 | Pro | Thr | Gly | Pro | Leu 10 | Pro | Gln | Ser | Phe | Leu 15 | Leu |
| Lys | Cys | Leu | Glu 20 | Gln | Met | Arg | Lys 25 | Val | Gln | Ala | Asp | Gly 30 | Thr | Ala | Leu |
| Gln | Glu | Thr 35 | Leu | Cys | Ala | Thr | His 40 | Gln | Leu | Cys | His | Pro 45 | Glu | Glu | Leu |
| Val | Leu 50 | Leu | Gly | His | Ala | Leu 55 | Gly | Ile | Pro | Gln | Pro 60 | Pro | Leu | Ser | Ser |
| Cys 65 | Ser | Ser | Gln | Ala | Leu 70 | Gln | Leu | Met | Gly | Cys 75 | Leu | Arg | Gln | Leu | His 80 |
| Ser | Gly | Leu | Phe | Leu 85 | Tyr | Gln | Gly | Leu | Leu 90 | Gln | Ala | Leu | Ala | Gly 95 | Ile |
| Ser | Pro | Glu | Leu 100 | Ala | Pro | Thr | Leu | Asp 105 | Thr | Leu | Gln | Leu | Asp 110 | Thr | Thr |
| Asp | Phe | Ala 115 | Ile | Asn | Ile | Trp | Gln 120 | Gln | Met | Glu | Asp | Leu 125 | Gly | Met | Ala |
| Pro | Ala 130 | Val | Pro | Pro | Thr | Gln 135 | Gly | Thr | Met | Pro | Ala 140 | Phe | Thr | Ser | Ala |
| Phe | Gln | Arg | Arg | Ala | Gly | Gly | Val | Leu | Val | Ala | Ser | Asn | Leu | Gln | Ser |

```
         145                      150                      155                      160
Phe  Leu  Glu  Leu  Ala  Tyr  Arg  Ala  Leu  Arg  His  Phe  Ala  Lys  Pro
                         165                      170                      175
```

( 2 ) INFORMATION FOR SEQ ID NO:6:

( i ) SEQUENCE CHARACTERISTICS:
        ( A ) LENGTH: 175 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Met  Thr  Pro  Leu  Gly  Pro  Ala  Ser  Ser  Leu  Pro  Gln  Ser  Phe  Leu  Leu
 1                    5                        10                       15

Lys  Cys  Leu  Glu  Gln  Val  Arg  Lys  Ile  Gln  Gly  Asp  Gly  Ala  Ala  Leu
               20                       25                       30

Gln  Glu  Lys  Leu  Cys  Ala  Thr  Tyr  Lys  Leu  Cys  His  Pro  Glu  Glu  Leu
          35                       40                       45

Val  Leu  Leu  Gly  His  Ser  Leu  Gly  Ile  Pro  Trp  Ala  Pro  Leu  Ser  Ser
     50                       55                       60

Cys  Pro  Ser  Gln  Ala  Leu  Gln  Leu  Ala  Gly  Cys  Leu  Ser  Gln  Leu  His
65                       70                       75                       80

Ser  Gly  Leu  Phe  Leu  Tyr  Gln  Gly  Leu  Leu  Gln  Ala  Leu  Glu  Gly  Ile
               85                       90                       95

Ser  Pro  Glu  Leu  Gly  Pro  Thr  Leu  Asp  Thr  Leu  Gln  Leu  Asp  Val  Ala
              100                      105                      110

Asp  Phe  Ala  Thr  Thr  Ile  Trp  Gln  Gln  Met  Glu  Glu  Leu  Gly  Met  Ala
          115                      120                      125

Pro  Ala  Leu  Gln  Pro  Thr  Gln  Gly  Ala  Met  Pro  Ala  Phe  Ala  Ser  Ala
     130                      135                      140

Phe  Gln  Arg  Arg  Ala  Gly  Gly  Val  Leu  Val  Ala  Ser  His  Leu  Gln  Ser
145                      150                      155                      160

Phe  Leu  Glu  Val  Ser  Tyr  Arg  Val  Leu  Arg  His  Leu  Ala  Gln  Pro
                    165                      170                      175
```